United States Patent
Sakamoto et al.

(10) Patent No.: US 8,625,099 B2
(45) Date of Patent: Jan. 7, 2014

(54) PARTICLE CONCENTRATION MEASURING DEVICE

(75) Inventors: Kazuhiko Sakamoto, Chino (JP); Hiroshi Kawakita, Chino (JP); Hiroyuki Okami, Chino (JP); Yusuke Iso, Chino (JP); Ryuta Okamoto, Tokyo (JP)

(73) Assignee: Shin Nippon Air Technologies Co., Ltd., Tokyo (JP)

( * ) Notice: Subject to any disclaimer, the term of this patent is extended or adjusted under 35 U.S.C. 154(b) by 113 days.

(21) Appl. No.: 13/160,100

(22) Filed: Jun. 14, 2011

(65) Prior Publication Data

US 2011/0304850 A1    Dec. 15, 2011

(30) Foreign Application Priority Data

Jun. 15, 2010 (JP) .................... 2010-135838

(51) Int. Cl.
*G01N 21/61* (2006.01)

(52) U.S. Cl.
USPC .......................................... 356/438; 356/337

(58) Field of Classification Search
USPC .................... 356/335–343, 432–440
See application file for complete search history.

(56) References Cited

U.S. PATENT DOCUMENTS

| | | | |
|---|---|---|---|
| 4,728,190 A | | 3/1988 | Knollenberg |
| 4,739,177 A | | 4/1988 | Borden |
| 5,121,988 A | * | 6/1992 | Blesener et al. ............ 356/442 |
| 5,153,665 A | * | 10/1992 | Weinstein ..................... 356/28 |
| 5,426,501 A | * | 6/1995 | Hokanson et al. ............ 356/335 |
| 5,835,211 A | * | 11/1998 | Wells et al. ................... 356/336 |
| 6,151,113 A | * | 11/2000 | O'Donohue et al. ......... 356/338 |
| 6,211,956 B1 | * | 4/2001 | Nicoli ........................... 356/337 |
| 7,265,832 B2 | * | 9/2007 | Montgomery et al. ....... 356/338 |
| 7,417,732 B2 | * | 8/2008 | Iwa et al. ...................... 356/336 |
| 2003/0016357 A1 | * | 1/2003 | Shofner et al. ............... 356/337 |
| 2004/0104681 A1 | * | 6/2004 | Mitrovic .................. 315/111.21 |
| 2010/0134796 A1 | | 6/2010 | Arakawa et al. |

FOREIGN PATENT DOCUMENTS

| | | |
|---|---|---|
| JP | S61-223630 | 10/1986 |
| JP | H09-79967 A | 3/1997 |
| JP | H09-145616 A | 6/1997 |
| JP | H11-352059 A | 12/1999 |
| JP | 2000-019112 A | 1/2000 |
| JP | 2003-14580 A | 1/2003 |
| JP | 2003-42934 A | 2/2003 |
| JP | 2005-077251 A | 3/2005 |
| JP | 2005-114664 A | 4/2005 |
| JP | 2006-133110 A | 5/2006 |
| JP | 2009-2733 A | 1/2009 |

* cited by examiner

*Primary Examiner* — Hoa Pham

(74) *Attorney, Agent, or Firm* — Renner Kenner; Arthur M. Reginelli

(57) ABSTRACT

A particle concentration measuring device includes: a measurement region formation part which has a wall (10) of substantially ring-form and through an inner opening of which gas relatively flows orthogonally; a light curtain forming unit (12A, 12B) forming a planar light curtain (FL) in the inner opening: a particle detecting unit (15) receiving scattered light from particles passing through the light curtain (FL) to detect the particles; and a calculating unit (22) calculating particle concentration based on the total number of the particles detected by the particle detecting unit (15) in a volume of an airflow passing through the light curtain (FL) in a unit time.

5 Claims, 7 Drawing Sheets

PARTICLE CONCENTRATION MEASURING DEVICE

BACKGROUND OF THE INVENTION

1. Field of the Invention

The present invention relates to a particle concentration measuring device, more particularly, to a particle concentration measuring device capable of measuring particle concentration with high accuracy at a place in a clean room where a uniform unidirectional flow is ensured, or at other places.

2. Description of the Related Art

In a clean room and the like, measuring or managing concentration of particles such as dust floating in the air (the number of particles in a unit volume) is an important issue.

As this kind of conventional device measuring concentration of particles (particle concentration), the most popularly known one is a device of a sampling suction type that sucks the air through a sampling tube by the operation of a suction pump and finds the number of particles in the air by a light-scattering method. However, the need to install the sampling tube at a measurement target position makes this device unable to measure in a space where the flow changes due to the suction and thus a degree of freedom in its measurement place is low.

Further, in the measurement by this device, an airflow velocity and a suction speed are desirably equal to each other, but it is practically difficult to adjust the operation of the suction pump so as to make them equal to each other, and in addition, increasing the suction time in order to obtain a sufficient volume of the sampled air results in the detection of not only particle concentration at the target point but also particle concentration in a space far more upwind than this point, which has been a cause of deteriorating detection accuracy.

Another proposed device is a device measuring particle concentration from a remote place by a laser radar method. This device synchronizes a laser pulse and a shutter timing of a camera and measures the particle concentration by counting scattered lights of particles in a volume defined by a laser pulse width and a shutter speed.

The aforesaid device measuring the concentration from a remote place by the laser radar method is suitable for measuring the concentration of a large volume of particles in the atmosphere or the like from a remote place, but in an indoor space or the like, the laser pulse width and the shutter time become extremely short as a sampling volume becomes small, which makes it difficult to obtain light intensity large enough for the measurement, and thus the device is not practically capable of measuring small particles of 1 μm or less.

There have been also known an air impurity monitor which is capable of measuring impurity concentration in an atmosphere in a clean room automatically, speedily, and continuously and which is easy to handle and costs low (Japanese Patent Application Laid-open No. Hei 9-145616) and a dust measuring device used in a clean room and structured to receive dust by a dust collection sheet (Japanese Patent Application Laid-open No. 2003-42934).

The device of Japanese Patent Application Laid-open No. Hei 9-145616 sucks impurities to a hermetically closable impurity capturing vessel to supply the impurities into ultra-pure water, and it not only has the same drawback as that of the aforesaid device sucking the air through the sampling tube but also has a complicated device structure. Further, the device of Japanese Patent Application Laid-open No. 2003-42934 is structured to receive the dust by the dust collection sheet, and is not suitable for measuring particle concentration (the number of particles in a unit volume).

SUMMARY OF THE INVENTION

The present invention seeks to provide a particle concentration measuring device capable of measuring particle concentration with high accuracy at a place in a clean room where a uniform unidirectional flow is ensured, or at other places.

A particle concentration measuring device according to claim 1 includes:

a measurement region formation part which has a wall of substantially ring-form defining an inner opening through which gas flows relatively orthogonally;

a light curtain forming unit forming a planar light curtain in the inner opening;

a particle detecting unit receiving scattered light from particles passing through the light curtain to detect the particles; and a calculating unit calculating particle concentration based on a total number of the particles detected by the particle detecting unit in a volume of an airflow passing through the light curtain in a unit time.

The particle concentration measuring device according to the present invention is installed, for example, in a clean room of a unidirectional flow type (or a straight flow type) in which an airflow flows uniformly in one direction, or at a place of a flow supplying a laminar flow. In this case, in order to physically demarcate a measurement region, the wall of substantially ring-form demarcates the measurement region, and through the opening thereof, gas relatively flows orthogonally.

The light curtain forming unit forms the planar light curtain in the whole or part of the opening, and the particle detecting unit receives the scattered light from the particles passing through the light curtain to be capable of detecting the particles. As a result, by calculating a volume of the airflow passing through the light curtain in a unit time by an appropriate method (for example, the volume of the airflow can be calculated based on the velocity of the airflow, the area of a measurement region, and the light-receiving time), it is possible for the calculating unit to calculate the particle concentration based on the total number of the particles detected by the particle detecting unit in the calculated volume.

In the present invention, demarcating the space by the wall of substantially ring-form makes it possible to easily find the volume of the airflow passing through the light curtain in a unit time, and further forming the planar light curtain in the whole or part of the demarcated region and receiving the scattered light from the particles passing through the light curtain to detect the particles makes it possible to calculate the particle concentration based on the total number of the particles in the volume of the airflow passing through the light curtain in a unit time.

Therefore, in detecting particles at a place in a clean room where a uniform unidirectional flow is ensured or at a place of a flow supplying a laminar flow, the airflow is not disturbed as it has been in the conventional example and the light-receiving time can be increased, which makes it possible to measure particle concentration with high accuracy and to detect fine particles of 1 μm or less as will be described later.

A particle concentration measuring device according to claim 2 is provided at a place where an airflow flows uniformly through the inner opening, wherein positions of the measurement region formation part, the light curtain forming unit, and the particle detecting unit are fixed.

At a place where the airflow uniformly flows through the inner opening, the positions of the measurement region formation part, the light curtain forming unit, and the particle detecting unit may be fixed. This is because the volume of the airflow can be calculated based on, for example, the velocity of the airflow, the area of the inner opening, and the light-receiving time.

A particle concentration measuring device according to claim 3 is structured such that the measurement region formation part, the light curtain forming unit, and the particle detecting unit linearly move as a unit.

For example, in a clean room of a non-straight flow type which is not a unidirectional flow type (or a straight flow type) where the airflow flows uniformly in one direction or in a case where particles are simply floating without an airflow being generated, the volume of gas cannot be accurately found or is not known.

Here, linearly moving the measurement region formation part results in that the gas "relatively" flows orthogonally through the inner opening demarcated by the wall even if the airflow is not generated, which makes it possible to find the volume of the airflow passing through the light curtain in a unit time.

A particle concentration measuring device according to claim 4 is structured such that, in the form of claim 3, the particle detecting unit is disposed at a position deviated from and not intersecting with an orthogonal line passing through the inner opening, and a light-receiving axis of the particle detecting unit is inclined with respect to the light curtain.

If the particle detecting unit is on the orthogonal line passing through the inner opening, the airflow is disturbed due to the presence of the particle detecting unit. This leads to a measurement error. Therefore, by adopting the form in which the particle detecting unit is disposed at a position deviated from and not intersecting with the orthogonal line passing through the inner opening and the light-receiving axis of the particle detecting unit is inclined with respect to the light curtain, it is possible to detect the particles without disturbing the airflow.

A particle concentration measuring device according to claim 5 is structured such that:

the particle detecting unit is disposed at a position deviated from and not intersecting with an orthogonal line passing through the inner opening t and a light-receiving axis of the particle detecting unit is inclined with respect to the light curtain; and the light curtain forming unit forms the light curtain on an upstream side of a flow of the gas, a plurality of movable vanes the inclination angles of which with respect to the flow of the gas are variable are provided on a downstream side of the flow of the gas, and the movable vanes have poor or no light transmitting property.

When the particle detecting unit detects particles by receiving scattered light from the particles, it is difficult to distinguish the scattered light from the background of the measurement (light-receiving) region unless the background is in dark color. A possible solution to this is to provide a nonreflective background at the rear of the measurement region formation part, but this will be a cause of obstructing the flow of the airflow through the opening inner part.

On the other hand, especially in the form where the light-receiving axis of the particle detecting unit is inclined with respect to the light curtain, by providing the plural movable vanes having poor or no light transmitting property as the background on the downstream side of the flow of the gas and inclining the movable vanes with respect to the flow of the gas, the airflow is not obstructed, and in addition, it is possible for the movable vanes to have the same function as that of the nonreflective background.

A particle concentration measuring device according to claim 6 is structured such that the light curtain forming unit forms the light curtain on an upstream side of the flow of the gas, and movable vanes the inclination angles of which with respect to the flow of the gas are variable are provided on a downstream side of the flow of the gas.

In some case, the area as a measurement region in the inner opening may be small with respect to an area of the whole inner opening In this case, it is possible to adjust the flow of the airflow by adjusting the angle of a movable vane corresponding to a region where the flow is not needed or a region where the flow need not be uniform, such as making this movable vane inclined or orthogonal with respect to the flow of the gas.

As described above, in embodiments of the particle concentration measuring device according to the present invention, there is produced an excellent effect of enabling the highly accurate measurement of particle concentration at a place in a clean room where a uniform unidirectional flow is ensured, or at other places.

DETAILED DESCRIPTION OF THE PREFERRED EMBODIMENTS

Hereinafter, a first embodiment of a particle concentration measuring device according to the present invention shown in FIG. 1 to FIG. 3 will be described.

Figure 1:
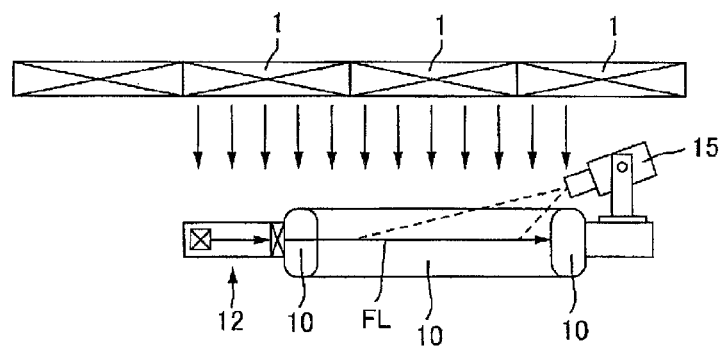
FIG. 1 is an explanatory view showing a disposition state of a particle concentration measuring device according to the present invention.

The particle concentration measuring device according to this embodiment shown in FIG. 1 is disposed horizontally in, for example, a region right under ceiling filters (HEPA filters) 1 of a clean room of a unidirectional flow type (or a straight flow type) in which an airflow flows uniformly in one direction, and is used to measure the concentration of particles such as dust.

Figure 2:
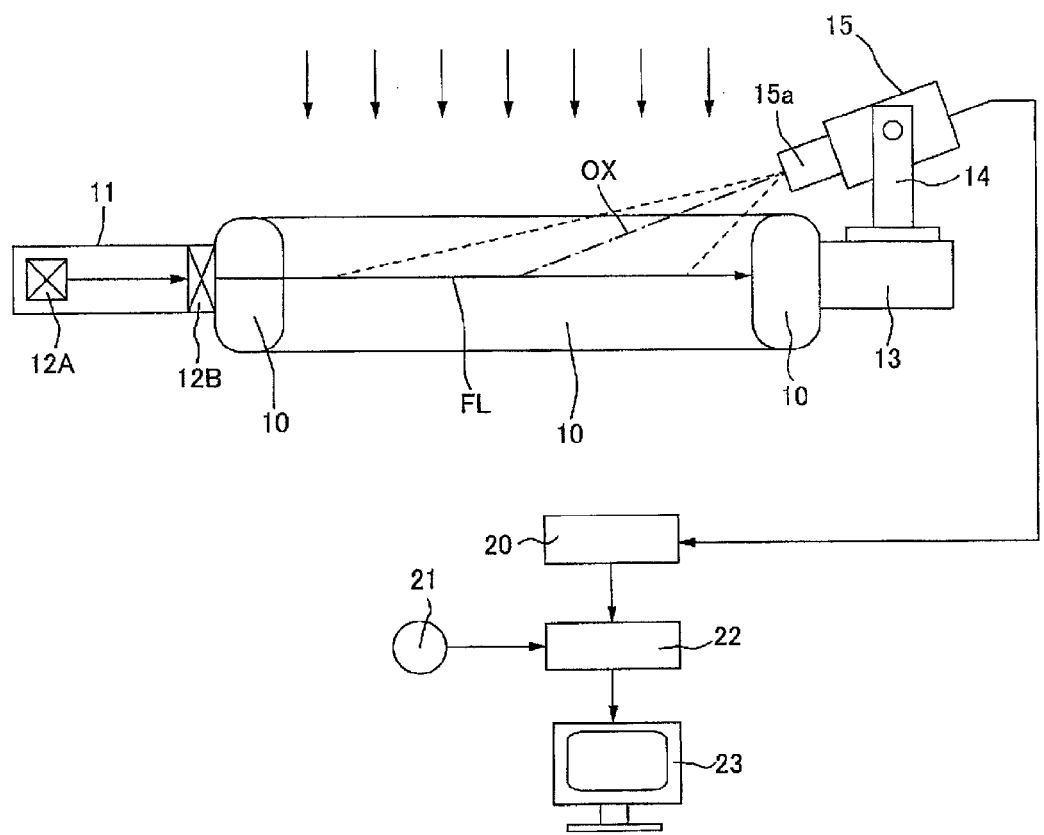
FIG. 2 is a schematic front view, partly in section, showing a first embodiment of the particle concentration measuring device according to the present invention.
Figure 3:
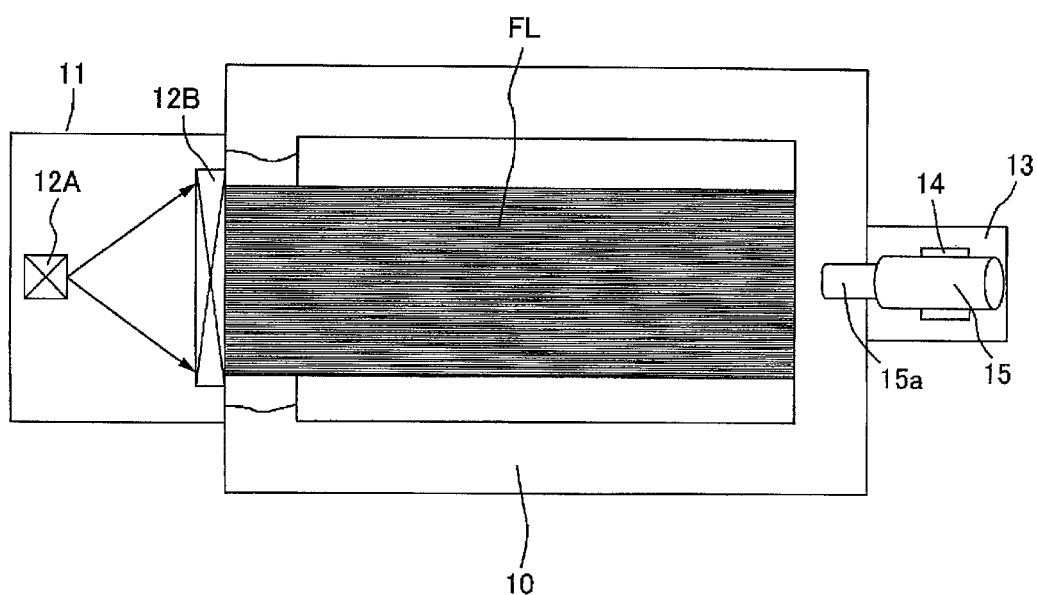
FIG. 3 is a schematic plane view showing the first embodiment of the particle concentration measuring device.

The particle concentration measuring device has a wall or partition 10 which is formed in a substantially ring form for example, in a rectangular frame shape as shown in FIG. 2 and FIG. 3, and through an inner opening part demarcated by the partition 10, clean air flows orthogonally, that is, flows down vertically, and a measurement region formation part is formed by this partition 10.

A casing 11 is provided adjacently to the partition 10, and in the casing 11, there are provided a light curtain (which may also be referred to as a film) forming unit including a laser light scanning unit 12A which generates a scanning laser light and a collimating unit 12B converting the scanning laser light into a planar light curtain FL to form the planar light curtain which is to be supplied to the opening inner part of the partition 10.

An imaging unit 15 is disposed on a support 13 integrally formed with a portion of the partition 10 opposite the casing 11 while being supported by a support bracket 14.

The imaging unit 15 constitutes a particle detecting unit receiving scattered light from particles passing through the light curtain FL to detect the particles.

A detection signal of particle scattered light from the imaging unit 15 is received by an image signal processor 20, where it is determined whether a light-receiving signal at a certain place represents a particle, and the particle signal is given to a particle concentration calculating unit 22. The particle concentration calculating unit 22 is supplied with an airflow velocity from an airflow velocity detector 21 provided at an appropriate position, and calculates particle concentration based on the total number of the particles detected by the particle detecting unit in a volume of the airflow passing through the light curtain FL in a unit time. The data of calculated particle concentration is displayed on a display device 23 such as a CRT and is also given to an airflow controller (not shown) of the clean room to be used for airflow control.

Figure 8:
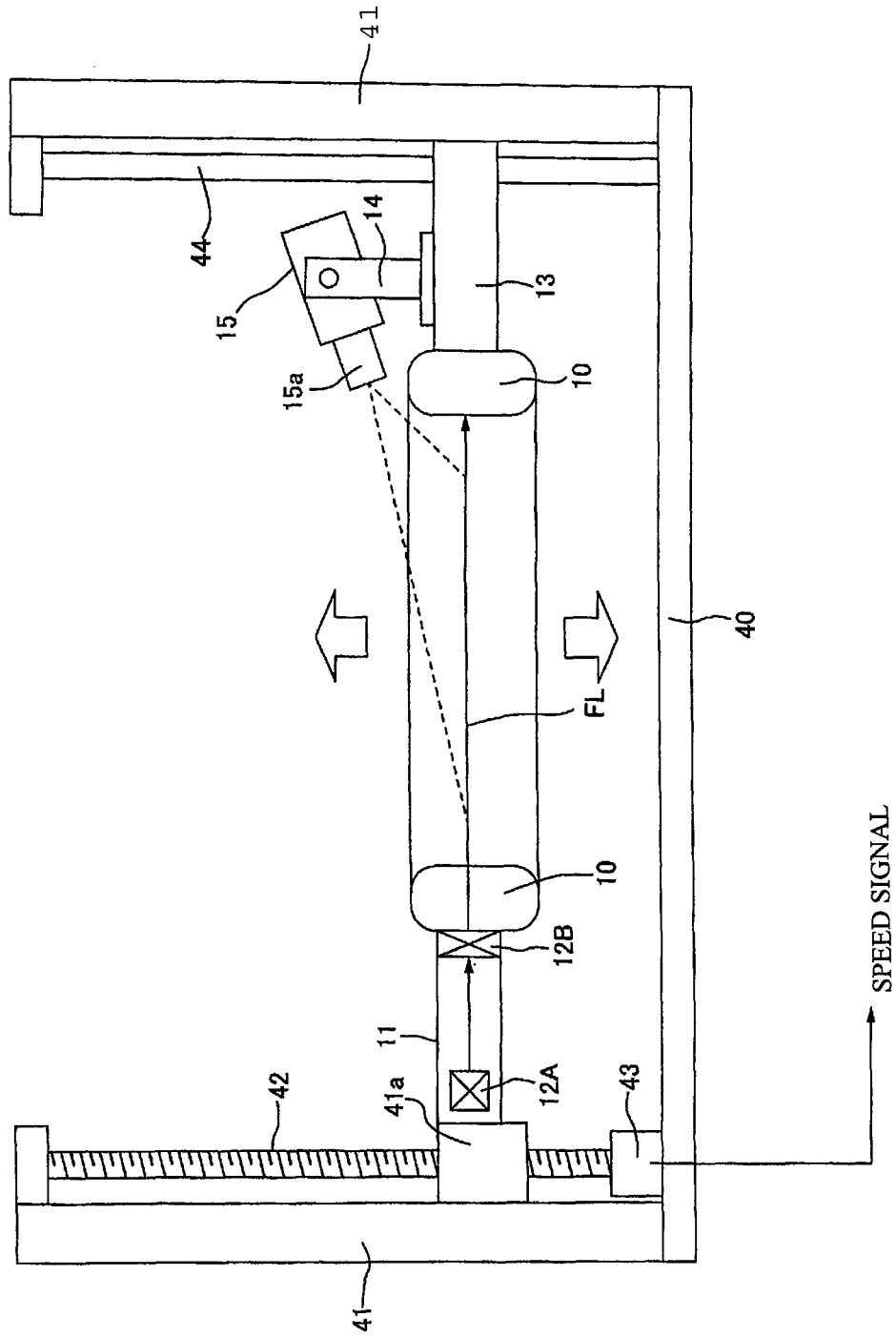
FIG. 8 is a schematic front view, partly in section, showing a third embodiment of the particle concentration measuring device according to the present invention.

The particle concentration c is calculated by the expression $c = n/(r \times v \times T)$. Here, definitions of the respective variables in the expression are as follows.

c: particle concentration
n: number of particles
r: area of a measurement region
v: airflow velocity
T: measurement time Incidentally, in a third embodiment (an embodiment in which the whole device linearly moves as a unit: an example in FIG. 8) of the particle concentration measuring device according to the present invention, it is possible to find the particle concentration c, with "v" being defined not as "airflow velocity" but as "movement speed" of the device.

Further, it is possible for the display device 23 to display a three-dimensional tomographic distribution of the particles per volume, with each unit area in the measurement region area r being correlated with the number of the particles in this unit area.

Though the partition 10 is formed as a ring, it need not be a completely closed ring but may be partially opened outward. Further, the partition 10 only needs to be in a substantially ring form and its shape may be a quadrangle such as a square other than the rectangle, any other polygon, a circle, or the like. The partition 10 is desirably formed to have a streamlined cross section as shown in FIG. 2 in order to prevent the disturbance of the airflow.

Figure 6:
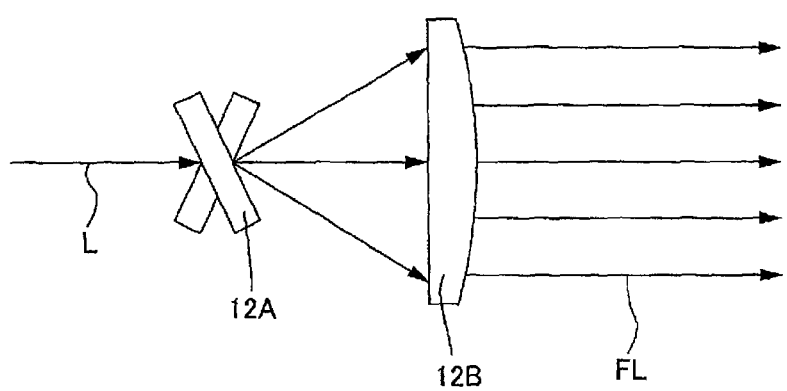
FIG. 6 is a plane view of still another example of the light curtain forming unit.

A simple example of the light curtain forming unit is an example where a galvano-mirror (laser light scanning unit) 12A receiving laser light L to scan a predetermined angle range and a semi-convex lens (collimating unit) 12B are used as shown in FIG. 6.

Figure 4:
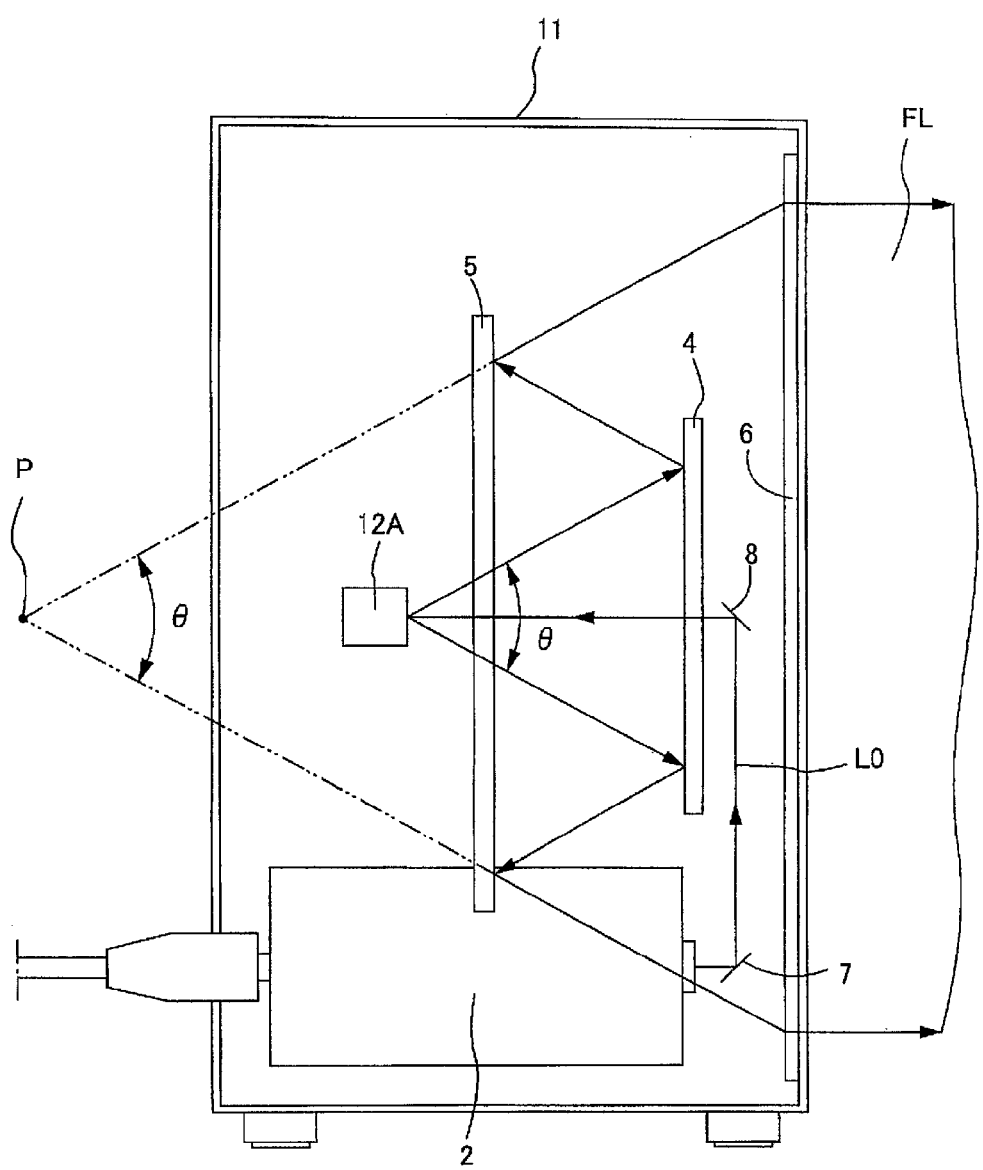
FIG. 4 is a schematic plane view of another example of a light curtain forming unit.
Figure 5:
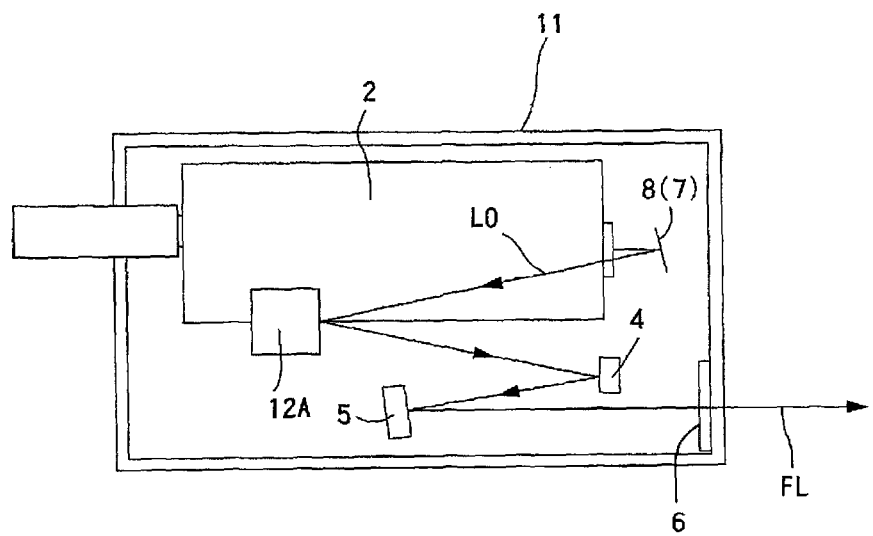
FIG. 5 is a schematic front view of the other example of the light curtain forming unit.

Another possible example is one shown in FIG. 4 and FIG. 5. The light curtain forming unit of this example includes a laser light generator 2, a scanning unit 12A such as a galvano-mirror, a first mirror 4, a second mirror 5, and a Fresnel lens 6. In this example, the first mirror 4, the second mirror 5, and the Fresnel lens 6 constitute the collimating unit 12B.

Laser light L0 emitted forward from the laser light generator 2, after being changed in angle by angle changing mirrors 7, 8 a detailed illustration of which is omitted, enters the scanning unit 12A, and the scanning unit 12A receives the linear laser light to perform the scanning so as to spread the laser light in a fan shape.

The laser light from the scanning unit 12A is reflected between the first mirror 4 and the second mirror 5 which face each other in parallel in a front and rear direction to become scanning light in a more widely spread fan shape. That is, the light reflected by the first mirror 4 enters the second mirror 5 and radiates forward at the second mirror 5. The radiant light passes through the Fresnel lens 6 to radiate into the air as collimated scanner beam light. Using a plastic lens as the Fresnel lens 6 is cost-advantageous.

Consequently, even if a swing angle θ is formed by the scanning unit 12A, it is possible to emit the light curtain FL as wide collimated scanner beam light as in a case where a scanning unit 12A is virtually installed at a rear position P shown in FIG. 4.

As the scanning unit, a galvano-mirror, a resonant mirror, a polygon mirror, or the like is usable. The swing angle θ by the scanning unit 12A is appropriately selectable or adjustable. As a result, the width of the collimated scanner beam light can be adjusted.

The imaging unit 15 constituting the particle detecting unit is disposed at a position deviated from and not intersecting with an orthogonal line (in the shown example, a vertical line) passing through the opening inner part. This makes it possible to detect the particles while preventing the airflow from being disturbed by the presence of the imaging unit 15. Further, a light-receiving axis OX of a light-receiving part 15a of the imaging unit 15 is inclined with respect to the light curtain FL.

The light curtain FL not only can be formed in the whole opening inner part of the partition 10 but also can be formed to have a narrow width as shown in FIG. 3. Further, a light-receiving (imaging) region in the front and rear direction may be part of the opening inner part of the partition 10 in terms of the front and rear direction instead of the whole thereof as shown in FIG. 2.

Even if a processing range of a captured image of the imaging unit 15 is not the whole opening inner part of the partition 10, no problem occurs in deciding "the area r of the measurement region" because a positional relation between the partition 10 and the light curtain FL is known in advance as advance information.

In the above example, the imaging unit 15 is provided on an upstream side of the clean air flow in terms of the partition 10 or the light curtain FL, but may be provided on a downstream side thereof.

According to the foregoing embodiment, when the particles are detected at a place in a clean room where a uniform unidirectional flow is ensured, at a place of a flow supplying a laminar flow, or the like, the airflow is not disturbed as it has been in the conventional example and the light-receiving time can be increased, which makes it possible to measure particle concentration with high accuracy and to detect fine particles of 1 μm or less as will be described later.

For reference's sake, an airflow containing PSL standard particles (particle size 0.5 μm) used for the calibration of a particle counter were blown out from the ceiling filters 1 of the clean room by the device shown in FIG. 1 to FIG. 3. At this time, a probe of the particle counter was installed under the partition 10 and all the PSL standard particles were trapped.

Figure 9:
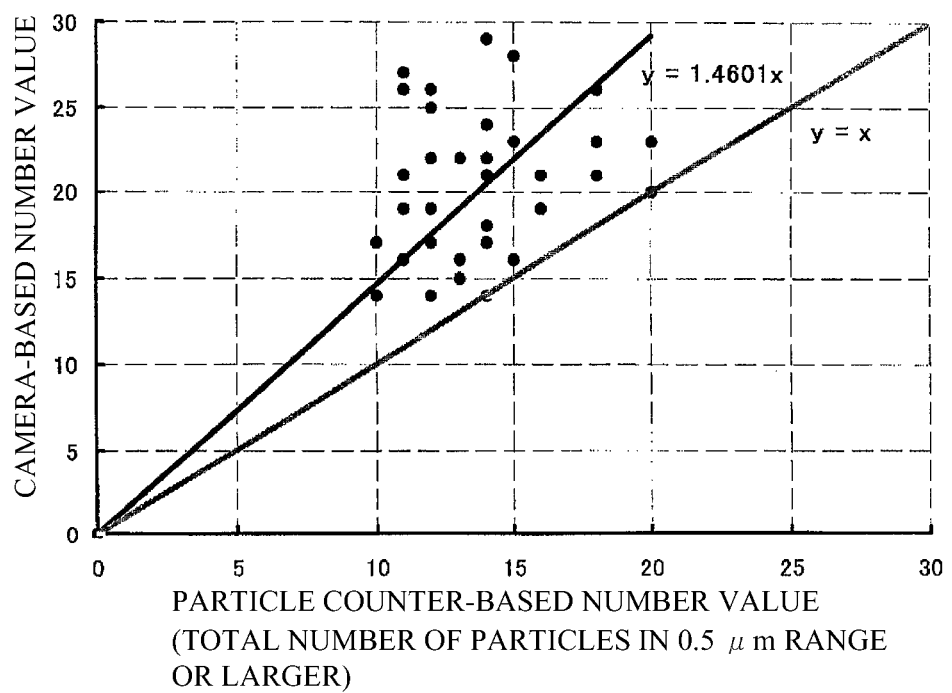
FIG. 9 is a chart showing a graph representing the result of comparison between values of the number of fine particles counted from a captured image of a camera imaging unit and values of the total number of particles in a 0.5 µm range or larger counted by a particle counter.

The result of the comparison between values of the number of fine particles counted from a captured image of the camera imaging unit 15 and values of the total number of particles in a 0.5 μm range or larger counted by the particle counter is shown in FIG. 9. Plot points are measured values, y=1.4601x is an approximate expression of the measured values according to the present invention, and y=x is a line in a case where the values of the total number of the particles in the 0.5 μm range or larger counted by the particle counter are equal to the values of the camera-based number. Since the points of the approximate expression y=1.4601x of the present invention are above the points of y=x, it can be confirmed that the particles of 0.5 μm or larger can be surely counted.

Figure 7:
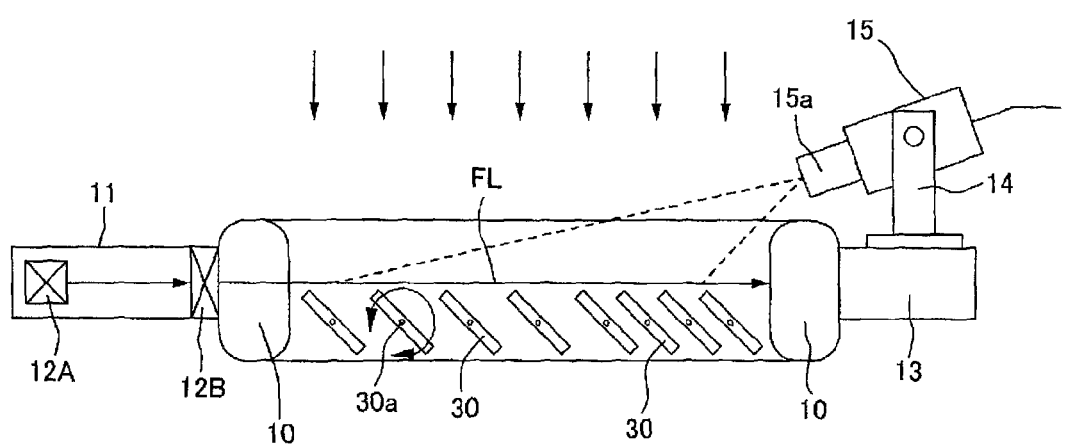
FIG. 7 is a schematic front view, partly in section, showing a second embodiment of the particle concentration measuring device according to the present invention.

FIG. 7 is a schematic front view, partly in section, showing a second embodiment of the particle concentration measuring device according to the present invention.

A plurality of movable vanes 30, 30 . . . which are movable around a support center 30a so that their inclination angles with respect to the flow of the gas are variable are provided on a downstream side of the flow of the gas in terms of the light curtain FL, and the movable vanes 30, 30 . . . have poor or no light transmitting property. That is, those made of a material in dark color similar to that of a nonreflective background or those surface-treated are used.

When the imaging unit 15 (particle detecting unit) receives scattered light from particles to detect the particles, it is difficult to distinguish the scattered lights from the background of a measurement (light-receiving) region unless the background is in dark color. A possible solution to this is to provide a nonreflective background at the rear of the measurement region formation part, but this will be a cause of obstructing the flow of the airflow through the opening inner part.

On the other hand, by providing the plural movable vanes 30, 30 . . . having poor or no light transmitting property as the background on the downstream side of the flow of the gas in terms of the light curtain FL and inclining them with respect to the flow of the gas as in this embodiment, the airflow is not obstructed, and in addition, it is possible for the movable vanes 30, 30 . . . to have the same function as that of the nonreflective background.

In this case, intervals between the movable vanes 30, 30 . . . each can be appropriately decided. For example, by narrowing the interval between some of the movable vanes 30, 30 or by increasing the inclination angle of some of the movable vanes 30, 30 with respect to the airflow, it is possible to prevent the airflow from flowing into this region.

Incidentally, the group of the movable vanes 30, 30, . . . not only can be provided in the partition 10 but also can be disposed on the downstream side of the flow of the gas in terms of the partition 10, being supported by another support member.

Next, the third embodiment of the particle concentration measuring device according to the present invention will be described in detail.

For example, in a clean room of a non-straight flow type not of a unidirectional flow type (or a straight flow type) where an airflow flows uniformly in one direction or in a case where an airflow is not generated and particles are simply floating, a volume of gas cannot be accurately found or is not known.

Therefore, linearly moving the measurement region formation part as in the third embodiment of the particle concentration measuring device according to the present invention results in that the gas "relatively" flows orthogonally through the inner opening demarcated by the partition 10 even if the airflow is not generated, which makes it possible to find the volume of the airflow passing through the light curtain FL in a unit time.

The particle concentration measuring device according to the third embodiment is structured such that the measurement region formation part, the light curtain forming unit, and the particle detecting unit linearly move as a unit as shown in FIG. 8.

Concretely, posts 41, 41 are provided upright on a base 40, and a slide part 41a is fitted in a guide groove (not shown) of the post 41. A ball screw shaft 42 rotated by a driving motor 43 is screwed to the slide part 41a, and the ball screw shaft 42 is rotated by the driving motor 43 so that the slide part 41a moves up and down along the guide groove of the post 41. The slide part 41a is integrated with the casing 11, and as a result, a main part of the device including the partition 10 and the imaging unit 15 moves up and down. In this case, a guide shaft 44 fixed to the post 41 is loosely fitted to a support 13, and this structure stabilizes the up/down movement.

As the imaging unit 15 (particle detecting unit) of the present invention, it is preferable that a pickup tube camera is a pickup tube camera using especially an avalanche pickup tube. Further, it is also preferable to provide an analog differentiator applying analog differentiation processing to a pickup image signal sent from the pickup tube camera, and detect aerosol based on the image having subjected to the differentiation processing of the analog differentiator. Further, it is also preferable that a lens hood shading a region except the detection target region so that this region is not photographed is attached to a lens of the pickup tube camera. This structure can improve detection ability. Further, a CCD camera, a camera, and the like the resolution of which has become higher in recent years are also usable.

The light curtain forming unit of the present invention may be one using LED light instead of the laser light.

Also adoptable is a structure in which, if necessary, a light trap (not shown) is provided in the partition 10 at a part receiving the light curtain FL so as to prevent the reflection of the light received by the light curtain FL.

The present invention is usable for measuring particles such as dust not only in a clean room but also in a factory facility where a laminar flow is ensured, and is applicable to all the fields requiring clean space, such as fields of semiconductor, liquid crystal, drugs and medicine, food, and medical treatment.

The invention claimed is:

1. A particle concentration measuring device characterized by comprising:

a measurement region formation part which has a wall (10) of substantially ring-form defining an inner opening through which gas flows relatively orthogonally;

a light curtain forming unit (12A, 12B) forming a planar light curtain (FL) in the opening inner part;

a particle detecting unit (15) which uses a camera and receives scattered light from particles passing through the light curtain (FL) to detect the particles; and a calculating unit (22) calculating particle concentration based on a total number of the particles detected by the particle detecting unit (15) in a volume of an airflow passing through the light curtain in a unit time, by means of the expression $c=n/(r \times v \times T)$ wherein c is particle concentration;

n is number of particles;

r is area of a measurement region;

v is airflow velocity, but if a measurement region formation part move, v is movement speed of the measurement region formation part, and T is measurement time;

where the device is provided at a place where an airflow flows uniformly through the inner opening; and where positions of the measurement region formation part, the light curtain forming unit (12A, 12B), and the particle detecting unit (15) are fixed.

2. The particle concentration measuring device according to claim 1, characterized in that the measurement region formation part, the light curtain forming unit (12A, 12B), and the particle detecting unit (15) linearly move as a unit.

3. The particle concentration measuring device according to claim 2, characterized in that the particle detecting unit (15) is disposed at a position deviated from and not intersecting with an orthogonal line passing through the inner opening, and a light-receiving axis (OX) of the particle detecting unit is inclined with respect to the light curtain (FL).

4. The particle concentration measuring device according to claim 1, characterized in that:

the particle detecting unit (15) is disposed at a position deviated from and not intersecting with an orthogonal line passing through the inner opening and a light-receiving axis (OX) of the particle detecting unit (15) is inclined with respect to the light curtain (FL); and the light curtain forming unit forms the light curtain (FL) on an upstream side of a flow of the gas, a plurality of movable vanes (30) the inclination angles of which with respect to the flow of the gas are variable are provided on a downstream side of the flow of the gas, and the movable vanes (30) have poor or no light transmitting property.

5. The particle concentration measuring device according to claim 1, characterized in that the light curtain forming unit forms the light curtain (FL) on an upstream side of the flow of the gas, and movable vanes (30) the inclination angles of which with respect to the flow of the gas are variable are provided on a downstream side of the flow of the gas.

* * * * *